United States Patent [19]
Aoyagi et al.

[11] Patent Number: 6,149,946
[45] Date of Patent: Nov. 21, 2000

[54] METHOD AND PRODUCT USING STURGEON NOTOCHORD FOR ALLEVIATING THE SYMPTOMS OF ARTHRITIS

[75] Inventors: Seiji Aoyagi, Kobe, Japan; Stephen J. DeMichele, Dublin, Ohio; Paul W. Johns, Columbus, Ohio; Terrence B. Mazer, Reynoldsburg, Ohio

[73] Assignee: Abbott Laboratories, Abbott Park, Ill.

[21] Appl. No.: 09/169,422

[22] Filed: Oct. 9, 1998

Related U.S. Application Data

[63] Continuation-in-part of application No. 08/887,432, Jul. 2, 1997, Pat. No. 5,849,336.

[51] Int. Cl.$^7$ .................................................. A61K 35/60
[52] U.S. Cl. ................................ 424/570; 514/2; 514/21; 514/62; 514/23; 530/356
[58] Field of Search ................................ 424/570; 514/2, 514/21, 62, 23; 530/356

[56] References Cited

U.S. PATENT DOCUMENTS

| | | | |
|---|---|---|---|
| 4,473,551 | 9/1984 | Schinitsky | 424/548 |
| 4,804,745 | 2/1989 | Koepff | 530/356 |
| 4,925,924 | 5/1990 | Silver et al. | 530/356 |
| 5,075,112 | 12/1991 | Lane | 424/434 |
| 5,399,347 | 3/1995 | Trentham et al. | 424/184.1 |
| 5,529,786 | 6/1996 | Moore | 424/464 |
| 5,709,887 | 1/1998 | Bryan et al. | 424/520 |
| 5,718,723 | 2/1998 | Matsuda et al. | 623/1 |
| 5,840,848 | 11/1998 | Sturrock et al. | 530/356 |

FOREIGN PATENT DOCUMENTS 0254289  1/1988  European Pat. Off. .

OTHER PUBLICATIONS

Weiner, et al., "Oral Tolerance: Immunologic Mechanisms and Treatment of Animal and Human Organ–Specific Autoimmune Diseases by Oral Administration of Autoantigens", Annu Rev Immunol 1994;12:809–837.

Trentham, et al., "Autoimmunity to Type II Collagen: An Experimental Model of Arthritis", J Exp Med 1977;146:857–868.

Courtenay, et al., "Immunization Against Heterologous Type II Collagen Induced Arthritis in Mice", Nature 1980;283–665.

Nagler–Anderson, et al., "Suppression of the Type II Collagen–Induced Arthritis by Intragastric Administration of Soluble Type II Collagen", Proc Natl Acad Sci USA 1986;83:7443–7446.

Thompson, et al., "Suppression of CIA by Oral Administration of Type II Colllagen: Changes in Immune and Arthritic Responses Mediated by Active Peripheral Suppression", Autoimmunity 1993;16:189–199.

Zhang, et al., "Suppression of Adjuvant Arthritis in Lewis Rats by Oral Administration of Type II Collagen", J Immunol 1990;145:2489–2493.

Paroli, et al., "A Pharmacological Approach to Glycosaminoglycans", Drugs Expth Clin Res VII(1) 9–20, 1991.

Miller, et al., "Characterization of Notochord Collagen", Biochemical and Biophysical Research Communications, vol. 60, No. 1, 1974.

Matthews, "Comparative Biochemistry of Chondroitin Sulphate–Proteins of Cartilage and Notochord", Biochem J., 1971, 125, 37–46.

*Primary Examiner*—Jean C. Witz
*Attorney, Agent, or Firm*—J. Michael Dixon; Nickki L. Parlet

[57] ABSTRACT

This invention provides a composition comprising notochord and extracts thereof in therapeutic amounts. The invention more specifically relates to a method of treating arthritis in mammals, more particularly rheumatoid arthritis in humans through the enteral administration of notochord, notochord extracts or mixtures thereof. In a preferred embodiment, collagen obtained from sturgeon is enterally administered to a human at from 1.0 $\mu$g to 1.05 gms per day.

8 Claims, No Drawings

METHOD AND PRODUCT USING STURGEON NOTOCHORD FOR ALLEVIATING THE SYMPTOMS OF ARTHRITIS

This is a continuation-in-part of U.S. patent application Ser. No. 08/887,432 filed on Jul. 2, 1997, now U.S. Pat. No. 5,849,336.

The present invention pertains to a method for treating the symptoms of arthritis in mammals and, more particularly, relates to the enteral administration of compositions comprising notochord and/or notochord extracts. The invention preferably uses sturgeon notochord, collagen derived from sturgeon notochord, or mixtures thereof to suppress the clinical manifestations of arthritis. The invention also relates to enteral compositions that contain notochord and its structural components to suppress and/or treat arthritis in mammals.

BACKGROUND OF THE INVENTION

Arthritis, and particularly rheumatoid arthritis (RA), is a painful and often crippling disease that initially results in swollen and inflamed joints, but often progresses to deform or completely destroy joints. This is a result of the body mistakenly attacking its own cartilage. Cartilage is a specialized kind of connective tissue which is found in human adults in three forms: hyaline or glossy cartilage; elastic cartilage; and fibrocartilage. Hyaline cartilage is the type found in the ventral ends of ribs, in joints, and in the walls of the larger respiratory passages. It is the hyaline cartilage that provides a low friction surface to prevent bone from rubbing on bone during motion. As arthritis progresses, cartilage is damaged and bone may also start to erode. This results in severe pain and ultimate destruction of the joint itself.

Arthritis is a group of diseases affecting joints and the component tissues. Several types of arthritis are recognized, and these can be divided into several groups by their clinical course or pathological manifestations. The most common form of arthritis is Osteoarthritis (OA). Osteoarthritis is mainly caused by mechanical damage to the joints, either by repetitive use of particular joints as seen in athletes and physical laborers, or by overloading structural joints as seen in the knee joints of obese individuals.

The second most common form of the disease is RA, which is a chronic multisystem disease of unknown cause. RA is characterized by chronic inflammation of the synovium associated with considerable erosion of both cartilage and bone, particularly in and around the joints. RA is currently understood as an autoimmune disease in which the pathological process appears to start by the presentation of an unknown "rheumatoid" self-antigen by an antigen presenting cell. Studies addressing family history indicate a genetic predisposition wherein a particular amino acid sequence in the third hypervariable region of the HLA-DR molecule is a major genetic element conveying susceptibility to RA. See Lipsky P E, "Rheumatoid Arthritis" in *Harrisons' Principles of Internal Medicine,* 13th ed. McGraw-Hill, Inc., New York, N.Y.

The T cell receptor on CD4+ T cells, which form the target of the antigen, also plays an important role in the inflammatory process. The presentation of the antigen causes the activation of CD4+ T cells, with the consequent secretion of cytokines such as interleukin-2 (IL-2) and interferon-g (IFN-g). These cytokines induce clonal expansion of the T cells and activation of the cytokine network. These cytokines trigger the production of endothelial adhesion molecules (such as ICAM-1) whose expression in rheumatoid synovium enhances the activation of inflammatory cells in the joints. See Vitali C, Sciuto M, Bombardieri S., "Immunotherapy in Rheumatoid Arthritis: A Review", *Int J Art Organs* 1993:16;196–200.

The modern therapy for arthritic conditions begins with nonsteroidal anti-inflammatory drugs such as aspirin, anthranilic acid, and ibuprofen; and more aggressive therapies involve disease-modifying antirheumatic drugs, such as D-penicillamine, methotrexate, and sulfasalazine. However, these treatments are often deficient in their efficacy and tolerability, causing a wide range of serious side effects. More severe forms of the disease may even require surgery.

(A) Oral Tolerance

Novel therapies for treating arthritis include immune response modifiers, gene therapy, enzyme inhibitors, monoclonal antibodies and dietary therapy. Dietary therapy for arthritis has received a great deal of publicity over the years. Although scientific basis, at present, for dietary remedies is still in doubt, there are valid reasons for considering whether dietary management can successfully modify disease activity as we better understand its etiology and pathology. "Oral tolerance" is a long recognized method to induce peripheral immune response. It was first described by Wells in 1911 as a state in which systemic anaphylaxis in guinea pigs was prevented by previous feeding of hen's egg proteins. See Wells H, "Studies on the Chemistry of Anaphylaxis III. Experiments with Isolated Proteins, Especially Those of Hen's Eggs", *J Infect Dis* 1911:9:147–151.

Particularly, oral tolerance is thought to be an ideal candidate to consider as a treatment of RA because of the etiology of RA as an autoimmune disease. Orally administered autoantigens have shown activity in several experimental autoimmune models including experimental autoimmune encephalomyelitis, uveitis, myasthenia, diabetes, and collagen- and adjuvant-induced arthritis. See Weiner H L, Friedman A, Miller A, Khoury S J, Al-Sabbagh A, Santos L, Sayegh M, Nussenblatt R B, Trentham D E, Hafler D A "Oral Tolerance: Immunologic Mechanisms and Treatment of Animal and Human Organ-Specific Autoimmune Diseases by Oral Administration of Autoantigens", *Annu Rev Immunol* 1994; 12:809–837.

The mechanism of how oral tolerance works is, at this time, unclear. The primary mechanisms by which an orally administered antigen induces tolerance are believed to be via the generation of active suppression or clonal anergy.

Collagen-induced arthritis (CIA) in experimental animals is the best known animal model for human RA. See Durie F H, Fava R A, Noelle R J, "Collagen-Induced Arthritis as a Model of Rheumatoid Arthritis" See *Clin Immu and Immupath* 1994; 73:11–18 and Staines N A, Wooley P H, "Collagen Arthritis-What Can it Teach Us?" *Brit J Rheum* 1994;33:798–807. It was first described by Trentham in 1977, see Trentham D E, Townes A S, Kang A H "Autoimmunity to Type II Collagen: An Experimental Model of Arthritis", *J Exp Med* 1977;146:857–868, and has been demonstrated to resemble human RA sufficiently to now be recognized as an important experimental tool. It is generally induced in susceptible strains of experimental animals (such as mice and rats) by immunization with heterologous type-II collagen (CII) isolated from a heterologous species. See Courtenay J S, Dallman M J, Dayyan A D, Martin A, Mosedale B, "Immunization Against Heterologous Type II Collagen Induced Arthritis in Mice", *Nature* 1980;283–665. In a susceptible strain of mice (DBA/1), immunization with CII initiates a combined humoral and cellular immune response targeted to joint tissues, where the antigen is predominantly located. Differences between the animal model and the human RA include:

(1) the model is an induced state and therefore does not occur spontaneously, as in humans;
(2) the model lacks many extra-articular manifestations of the human RA including subcutaneous nodules and pulmonary fibrosis; and
(3) the induction of the disease is of rapid onset in the model, which is different from humans in that it typically takes years.

Nevertheless, CIA is the best available animal model for human RA.

Intragastric administration of soluble Type II collagen (CII) prior to immunization with CII has been shown to suppress the incidence of CIA in DBA/1 Lac J mice, and WA/KIR rats. See Nagler-Anderson C, Bober L A, Robinson M E, Siskind G W, Thorbecke G J, "Suppression of the Type II Collagen-Induced Arthritis by Intragastric Administration of Soluble Type II Collagen", *Proc Natl Acad Sci USA* 1986;83:7443–7446 and Thompson H S G, Harper N, Devan D, Staines N A, "Suppression of CIA by Oral Administration of Type II Collagen: Changes in Immune and Arthritic Responses Mediated by Active Peripheral Suppression" *Autoimmunity* 1993;16:189–199.

Adjuvant-induced arthritis in Lewis rats was also shown to be suppressed by oral administration of soluble CII. See Zhang Z J, Lee C S Y, Lider O, Weiner H, "Suppression of Adjuvant Arthritis in Lewis Rats by Oral Administration of Type II Collagen", *J Immunol* 1990;145:2489–2493. The type of immunogen as well as the type of toleragen seems to be very important in exerting their effect in inducing and protecting the animal.

Cartilage is produced by cells called chondrocytes which synthesize and deposit around themselves a matrix of macromolecules that are known as collagen and proteoglycans. A remarkable function of cartilage tissue is that it replenishes itself in response to mechanical forces placed upon it.

A number of collagen types have been identified which provide the tough connective character of cartilage. The proteoglycans consist mainly of the high molecular weight molecules known as glycosaminoglycans (GAG) which include hyaluronic acid and chondroitin sulfate. GAGs were previously known as mucopolysaccharides. An overview of GAG's and their application in OA therapy is presented by Paroli, et al., in "A Pharmacological Approach to Glycosaminoglycans" *Drugs Expth. Clin. Res.* VII (1) 9–20 (1991).

A review of the various types of collagen can be found in Protein Profile, Vol. 1, 1994, pages 550–571; P. Sheterline, Ed. A review of the capacity of the immune system to discriminate between self and non-self structures and a discussion of how the immune system normally interacts with cartilage and how such interactions can lead to arthritis is set forth by Holmdahl, et al., in an article entitled "Autoimmune Recognition of Cartilage Collagens", *Annals of Medicine* 25:251–264, 1993. Type II collagen may be the best known oral toleragen for arthritis, however, there may exist other potential toleragens derived from non-cartilaginous tissues, such as vitreous humor, neural tubes and neural retina.

U.S. Pat. No. 5,529,786 to Moore discloses the use of animal tissue containing a therapeutic amount of CII for the treatment of RA in humans. This patent describes the animal tissue as preferably being chicken cartilage obtained from chickens less than about one year of age. Other animal tissues disclosed are bovine cartilage, the vitreous humor of eyes and a variety of other animals.

U.S. Pat. No. 4,473,551 to Schinitsky discloses a composition for the treatment of inflammatory disorders (such as RA, OA, acne, psoriasis and the like) which comprises animal cartilage and glucosamine. This patent describes the synergistic effect of a glucosamine and cartilages from whatever source derived, including shark and other marine dwellers, cattle, hogs, chicken and the like.

U.S. Pat. No. 5,075,112 to Lane discloses the use of finely divided shark cartilage for inhibiting tumor growth, arthritis, in particular RA, and inflammatory diseases with a vascular component. This patent does not suggest nor equate shark cartilage with any other mammal or avian cartilage.

U.S. Pat. No. 5,399,347 to Trentham, et al., discloses the use of a highly purified component from cartilage, whole CII protein, for the treatment of RA.

EP0254289B1 by Koepff, et al., discloses the treatment of arthritis through the administration of enzymatically hydrolyzed collagen from animal skins, animal bones, refined connective tissue or gelatin (Type I collagen) having an average molecular weight of from 10 to 80 KD.

Arthritis affects an estimated 40,000,000 people (15% of the population) in the United States. With an increasing survival time in the population, arthritis constitutes one of the greatest medical, social and economical problems in existence. The present invention furthers the state of the art of arthritis treatments and offers several advantages to presently accepted therapies.

(B) Notochord

As will be discussed and demonstrated below, notochord is a unique tissue to primitive groups of Osteichthyes, such as sturgeon and lamprey. Notochord appears in the post-gastrulation embryo as a very specialized mesoderm. In vertebrates, notochord serves as a core around which mesodermal cells gather to form the vertebrae (i.e., the notochord is the precursor of the vertebral column), but it disappears by the end of the embryonic stage. In the most primitive chordates, however, the notochord is retained as a primitive substitute for a vertebral column. Sturgeon and lamprey maintain a significant amount of notochord tissue in their vertebral column even in the adult stage. Regular mesoderm gives rise to the connective tissues of the body, such as hyaline cartilage and CII within. In fact, sturgeon notochord collagen may be a precursor form of CII, but it certainly is not CII. Notochord and cartilage are evolutionarily, developmentally, functionally, and anatomically different from each other. These differences in characteristics will be demonstrated below. The present invention relates to the use of intact and whole sturgeon notochord as well as its structural and chemical components (i.e., collagen derived from the notochord) for the treatment of RA and OA.

Support for the Applicant's position that notochord is different from cartilage can be found in an article by Miller and Mathews entitled, "Characterization of Notochord Collagen", published in *Biochemical and Biophysical Research Communications,* Vol. 60, No.1, 1974 and in an article published by Mathews entitled, "Comparative Biochemistry of Chondroitin Sulphate-Proteins of Cartilage and Notochord", published in *Biochem J.,* (1971), 125, 37–46. These publications discuss the characterization of sturgeon notochord by chromatographic properties, amino acid composition, carbohydrate content, cyanogen bromide cleavage products of the component a-chain, the molecular parameters of tryptic-chymotryptic hydrolysates of chondroitin sulfate-protein, and the fraction of chondroitin sulfate-protein in a caesium chloride density gradient. These analyses point out some of the chemical similarities, but more importantly, they evidence the distinct chemical and structural differences between cartilage and notochord.

The following Tables 1 and 2 are from the Mathews (1971) publication, supra, and highlight the differences of notochord collagen from ox cartilage and sturgeon cartilage.

TABLE 1

Molecular Parameters of Tryptic-Chymotryptic Hydrolysate of Chondroitin Sulfate-Protein and Products after Various Treatments

| Tissue | Molecular Parameter | TREATMENT | | | |
|---|---|---|---|---|---|
| | | None | NaOH | Papain | Pronase |
| Ox cartilage | [h] | 102 | 60 | 60 | 96 |
| | Mn | 43000 | 21000 | 21800 | — |
| | Mv | 56000 | 27000 | 27000 | 51000 |
| Sturgeon cartilage | [h] | 215 | 135 | 130 | 200 |
| | Mn | 50000 | 25400 | 23000 | — |
| | Mv | 66000 | 35000 | 34000 | 61000 |
| Sturgeon notochord | [h] | 38 | 25 | 23 | 33 |
| | Mn | 10000 | 5900 | 7100 | — |
| | Mv | 15000 | 8100 | 7400 | 12000 |

Mn viscosity molecular weight, was estimated from relationship $[h] = 3.1 \times 10^{-2} \, Mv^{0.74}$ for chondroitin sulphate A and $[h] = 5.8 \times 10^{-2} \, M^{0.74}$ for chondroitin sulphate C. (Mathews, 1971).

TABLE 2

Fractionation of Chondroitin Sulphate-Protein in a Caesium Chloride Density Gradient

| Source | Zone | Protein* | Chondroitin sulphate* | Protein in Chondroitin Sulphate-Protein from each Zone (%) |
|---|---|---|---|---|
| Ox cartilage | A | 10 | 0 | — |
| | B | 20 | <5 | — |
| | C | 70 | >95 | 10.4 |
| Sturgeon cartilage | A | 10 | 0 | — |
| | B | 10 | <4 | — |
| | C | 80 | >96 | 7.0 |
| Sturgeon Notochord | A | 40 | 6 | 69 |
| | B | 40 | 30 | 30 |
| | C | 20 | 64 | 21 |

The volumes and average densities at 20° C. of zones were: A, 3 ml, 1.42; B, 5 ml, 1.47; C, 4 ml, 1.54. Protein in chondroitin sulphate-protein from each zone was calculated from amino acid analysis. (Mathews, 1971)
*percentage of total

BRIEF DESCRIPTION OF THE DRAWINGS

FIG. 1 is a graphic representation of the data collected from the continued observations of Example IV.

DISCLOSURE OF THE INVENTION

The invention is generally directed to the enteral administration of notochord and extracts of notochord for the treatment of arthritis, specifically RA. The preferred source of notochord is sturgeon. Sturgeon notochord is readily available, efficacious and distinct from chicken and bovine cartilage. Sturgeon are presently raised in captivity for their flesh and, consequently, the quality (i.e., lack of pollutants) of the notochord can be controlled. One advantage in the use of sturgeon notochord and the extracts derived therefrom is the ease in combining the material with nutritional components that are also efficacious in the suppression of RA. A further advantage is that the intact sturgeon notochord is not subject to rigorous regulatory approval, as a drug would be.

As used herein and in the claims, the term "extracts of notochord" means the components that can be extracted from notochord using suitable extraction techniques, and include, for example, notochord collagens and GAG (including glucosamine and chondroitin sulfate).

There is disclosed a composition for oral consumption by mammals comprising at least one component selected from the group consisting of notochord, extracts of notochord and mixtures thereof. The composition may be in the form of a tablet, a pill, a capsule, a liquid (i.e., aqueous or oil suspension), a prepared food or food items, a nutritionally complete enteral formula or in the form of a nutritional supplement.

The compositions of the invention may contain from 10 μg to 1000 mg of notochord or notochord extract per gram of composition. When the composition is in the form of a liquid (i.e., aqueous suspension or oil suspension), the notochord component may comprise from 10 μg to 700 gms per liter; more preferably 10 μg to 500 gms per liter and most preferably 50 μg to 500 mg per liter. In a preferred embodiment, the liquid composition contains notochord collagen at a concentration of 10 μg to 10.5 gms per liter; 10 gms to 20 gms of glucosamine per liter; or 8 gms to 16 gms of chondroitin sulfate per liter.

In a further embodiment, the composition is in the form of a tablet, capsule or pill which contains from 1.0 μg to 2.0 gms of notochord or an extract of notochord. In a more preferred embodiment, the pill or tablet contains from 50 μg to 500 mg of the notochord and/or notochord extracts.

There is further disclosed a method for treating or reducing the incidence of the symptoms of arthritis, specifically RA in mammals, which comprises orally administering, to the mammal, a composition comprising at least one component selected from the group consisting of notochord, extracts of notochord and mixtures thereof in an amount and for a time effective to alleviate such symptoms.

In the method of the present invention, the amount of notochord consumed per day for a 70 kg human can range from 10 μg to 700 gms per day. More preferred, the dosage of notochord can range from 10 μg to 11 gms per day and most preferred from 10 μg to 1 gm per day. Collagen, as an extract from notochord, can be administered to a 70 kg human at from 1 μg to 1.05 gms per day. More preferred is the administration of 1 μg to 100 mgs of collagen purified from notochord per day. The most preferred dosage range of collagen purified from notochord is 1 μg to 10 mgs per day. Glucosamine purified from notochord is typically administered at a level of 1000 mgs to 2000 mgs per day per 70 kg human. The chondroitin sulfate purified from notochord is administered at a level of from 800 mgs to 1600 mgs per day. Those skilled in the art will appreciate that the rate of administration of the notochord containing composition will vary with many factors and that optimal dosage levels can be derived without undue experimentation.

The composition and method of the present invention are also applicable to non-human animals, such as dogs and horses. Many domesticated animals suffer from RA and they would benefit from the discovery set forth herein. The dosage levels for the 70 kg human set forth in the paragraph above can be converted to a dose range per kilogram of body weight, and that range can be used for animals. For example, the amount of notochord consumed per day for a 20 kg dog can range from 2.9 μg to 200 gms per day.

There is still further disclosed a process for the treatment of RA which comprises orally ingesting therapeutic quantities of notochord that has been removed from an animal of the Osteichthyes order or Acipenseridae family, preferably the Acipenser genus, and comminuted under clean or sterile conditions. The notochord is preferably treated with a sterilizing agent or by a sterilizing process prior to storage and ingestion. The oral administration of the notochord or a component thereof can be accomplished with other edible components such as in a nutritional supplement, a prepared food or in a nutritionally complete formula.

The three main species of sturgeon presently reared in the aquafarming industry are white sturgeon (*Acipenser transmontanus*), Italian sturgeon (*Acipenser naccarii*) and Siberian sturgeon (*Acipenser baeri*). Sturgeon is a cartilaginous fish of the family Acipenseridae, having no hard bones. Sturgeon are widely distributed in the north temperate zone of the planet.

Sturgeon is one of the oldest creatures found on earth, not having changed in the last 300 million years. White sturgeon, the largest freshwater fish in North America, can reach up to 2,000 lbs. Sturgeon, once sought after for caviar production, have recently become appreciated for the quality of their flesh. White sturgeon are now farm raised, indoors, in recycled well waters and are available from numerous commercial sources (e.g., Stolt Sea Farm California, L.L.C., Elverta, Calif. under the trade name of Belusa® White Sturgeon).

While the notochord of sturgeon are preferably disclosed herein for the treatment/reducing of arthritis, it is contemplated that the notochord of other chordates would also be useful. Chordates are animals of the phylum chordata and have, at least at some stage of their development, a notochord, a dorsally situated central nervous system, and gill clefts.

The sturgeon notochord and extracts thereof described in this invention have been shown by the inventors to be effective in treating experimentally induced arthritis in mice. As discussed above, the mice and rat models of arthritis are accepted in the medical community as highly predictive of efficacy in humans.

EXAMPLE I

Comparative Testing of Various Collagen-Containing Compositions

The chemical heterogenicity of sturgeon notochord from other collagen-containing tissues such as sturgeon cartilage, chicken cartilage and bovine cartilage is based on variations in hydroxylation, amino acid constitutents, glycosylation patterns, cross linking, conformation and the like. The following experiments (Experiments 1.1 to 1.4) were conducted to compare sturgeon notochord, chicken sternum cartilage and the collagen purified from each for amino acid profile, simulated gastric fluid digestion, trypsin digestion and hexosamine release.

Experiment 1.1: Amino Acid Profile

In this Experiment, the amino acid composition of sturgeon notochord was compared to the amino acid composition of chicken sternum cartilage. The samples of the sturgeon notochord were obtained from Stolt Sea Farm California, L.L.C. of Elverta, Calif. and the chicken cartilage was obtained from Tyson Farms, Inc. of Springdale, Ark.

An equal weight of each sample was frozen with liquid nitrogen and pulverized. The samples were hydrolyzed to amino acids in 22 hours at 110° C. in 6 M HCI. The amino acids were separated by ion exchange chromatography, derivatized with ninhydrin and determined with a colorimeter. The amino acid profile was determined using a Beckman 6300 model amino acid analyzer. The results of this analysis are set forth in Table 3 as residues per 100.

TABLE 3

Comparative Amino Acid Composition: Chicken Cartilage vs. Sturgeon Notochord (residues/100)

| Amino Acid | Chicken Cartilage | Sturgeon Notochord | % Difference |
|---|---|---|---|
| Aspartic acid | 6.06 | 5.95 | −2% |
| Threonine | 3.3 | 2.93 | −11% |
| Serine | 3.45 | 4.31 | 25%* |
| Glutamic acid | 9.72 | 10.23 | 5% |
| Proline | 10.05 | 10.92 | 9% |
| Glycine | 25.6 | 28.55 | 12% |
| Alanine | 9.35 | 8.21 | −12% |
| Cysteine | 0.39 | 0.16 | −59%* |
| Valine | 3.12 | 2.76 | −12% |
| Methionine | 1.52 | 1.43 | −6% |
| Isoleucine | 1.94 | 1.98 | 2% |
| Leucine | 4.23 | 4.09 | −3% |
| Tyrosine | 0.63 | 0.84 | 33%* |
| Phenylalanine | 2.01 | 1.48 | −26%* |
| Histidine | 1.17 | 0.96 | −18%* |
| Lysine | 2.75 | 1.92 | −30%* |
| Arginine | 5.57 | 4.95 | −11% |
| 4-Hydroxyproline (HPro) | 7.81 | 6.16 | −21% |
| 5-Hydroxylysine (HLys) | 1.53 | 2.16 | 41%* |
| Protein | 58% | 55% | |

*Deemed most significant; Tryptophan was not determined

From Table 3, it can be seen that the protein content on a dry weight basis is about the same for each sample, but the frequencies of serine, phenylalanine, lysine, 4-hydroxyproline (HPro), and 5-hydroxylysine (HLys) are most notably different.

In addition, the amino acid composition of collagen isolated from sturgeon notochord and bovine CII (bovine type II collagen from Sigma) was compared to the amino acid composition of chicken CII (chicken type II collagen from Sigma). The sturgeon notochord collagen was isolated as described in Example V, below. The results of this analysis are set forth in Table 4 as residues per 100.

TABLE 4

Comparative Amino Acid Composition (Residues per 100)

| | Chicken CII Sigma Lot #104H40111 | Bovine CII Sigma Lot #72H3799 | % Difference Between Chicken CII and Bovine CII | Sturgeon Notochord Collagen | % Difference Between Chicken CII and Sturgeon Notochord Collagen |
|---|---|---|---|---|---|
| Aspartic acid | 4.51 | 4.57 | 1% | 4.58 | 2% |
| Threonine | 2.67 | 2.21 | −17% | 2.42 | −9% |
| Serine | 2.22 | 2.52 | 14% | 3.64 | 64% |
| Glutamic acid | 8.59 | 8.56 | −0% | 9.45 | 10% |
| Proline | 11.32 | 12.38 | 9% | 12.55 | 11% |
| Glycine | 32.79 | 33.87 | 3% | 31.35 | −4% |
| Alanine | 9.79 | 10.26 | 5% | 8.63 | −12% |
| Cysteine | 0 | 0 | | 0 | |
| Valine | 1.94 | 1.97 | 2% | 1.94 | 0% |
| Methionine | 1.17 | 1.09 | −7% | 1.07 | −9% |
| Isoleucine | 1.04 | 1.1 | 6% | 1.52 | 46% |
| Leucine | 2.7 | 2.55 | − 6% | 3.49 | 29% |
| Tyrosine | 0.25 | 0.1 | −60% | 0.28 | 12% |
| Phenylalanine | 1.42 | 1.39 | −2% | 1.25 | −12% |

TABLE 4-continued

Comparative Amino Acid Composition (Residues per 100)

|  | Chicken CII Sigma Lot #104H40111 | Bovine CII Sigma Lot #72H3799 | % Difference Between Chicken CII and Bovine CII | Sturgeon Notochord Collagen | % Difference Between Chicken CII and Sturgeon Notochord Collagen |
|---|---|---|---|---|---|
| Histidine | 0.96 | 0.35 | −64% | 0.71 | −26% |
| Lysine | 1.61 | 1.88 | 17% | 1.62 | 1% |
| Arginine | 4.98 | 4.89 | −2% | 5.07 | 2% |
| 4-Hydroxyproline (HPro) | 9.8 | 8.6 | −12% | 7.56 | −23% |
| 5-Hydroxylysine (HLys) | 2.24 | 1.73 | −23% | 2.89 | 29% |

Tryptophan was not determined.

Table 4 summarizes the amino acid composition of purified chicken CII, bovine CII and sturgeon notochord collagen. The amino acid profiles of purified chicken CII and purified bovine CII are similar, however, there are substantial differences between purified chicken CII and purified sturgeon notochord collagen (i.e., serine, isoleucine and leucine).

Table 5 further illustrates significant differences between the two tissues (sturgeon notochord and chicken cartilage) and the three purified collagens (chicken CII, bovine CII, and sturgeon notochord collagen).

TABLE 5

Amino Acid Ratio Analysis

|  | HLys/HPro | HLys/Gly | Cumulative Absolute % Point Differences in Amino Acid Content[1] |
|---|---|---|---|
| Tissue |  |  |  |
| Chicken Cartilage | 0.20 | 0.06 |  |
| Sturgeon Notochord | 0.35 | 0.08 | 228[2] |
| Purified Collagen |  |  |  |
| Chicken CII | 0.23 | 0.07 |  |
| Bovine CII | 0.20 | 0.05 | 126[3] |
| Sturgeon Notochord Collagen | 0.38 | 0.09 | 263[3] |

[1]Absolute differences in amino acid composition between two tissues (or collagen) were calculated based on the values from Table 3 and 4 except for cysteine, tyrosine, and histidine as these amino acids are at less than 1% which could distort the percent differences between two tissues.
[2]Compared against chicken cartilage.
[3]Compared against chicken CII.

One skilled in the art in collagen chemistry will quickly appreciate the importance of HPro (for providing sites for cross-linking within the collagen) and HLys (for providing binding sites for glycans, glycosamines and the like which likely impact toleragenicity) and their relative levels (as this ratio is a major determinant of collagen types). Thus, differences in the levels of these amino acids are significant. In addition, the HLys to HPro ratio in cod type I collagen and bovine type III collagen is 0.11 and 0.07, respectively (data not shown).

Furthermore, the cumulative absolute percentage point differences between the collagens is greater between chicken CII and sturgeon notochord collagen (263 percentage points) than between chicken CII and bovine CII (126 percentage points). This means that bovine CII is closer to chicken CII in chemical composition than sturgeon notochord collagen is to chicken CII. Likewise, the difference in the amino acid composition between chicken cartilage and sturgeon notochord was 228 percentage points, indicating that they contain very different collagen from each other. These findings imply that sturgeon notochord and the collagen found within it are distinctly different from chicken cartilage and from type II collagen ("CII") in general.

As noted previously, these differences raise considerable doubt that sturgeon notochord would function in the same manner as chicken cartilage or chicken CII in a CIA model of RA. Experiments 1.2 to 1.4 reinforce the differences between notochord and other tissues.

Experiment 1.2: Gastric Fluid Digestion

In this Experiment, pulverized preparations of chicken cartilage and sturgeon notochord were suspended in USP Simulated Gastric Fluid (*United States Pharmacopoeia*, 23, 1994, page 2053) and incubated at 37° C. for 3 hours. A portion of each digest was filtered at specified intervals and the filtrates analyzed for HPro and HLys which are considered markers for collagen. The filtrates were also analyzed by size exclusion chromatography. The size exclusion chromatograms were generated on Hewlett-Packard Model 1090M instrument with Shodex Protein Column KW-803; 8×300 mm; 7 μm particle size; Waters P/N 35946 and a 20 μL Injection. A Mobile Phase of 600 volumes of water, 400 volumes of acetonitrile and 0.8 volumes of trifluoroacetic acid was used at ambient temperature at a Flow Rate of 0.3 mL/minute for 60 minutes. Detection was by U.V. absorbance at 214 nm.

Table 6 sets forth the collagen solubilization (measured as concentration of HPro and HLys versus time) in the digestion fluid after filtering through a 0.45 μm polysulfone membrane.

TABLE 6

Simulated Gastric Fluid Digestion Comparison
Sturgeon Notochord vs. Chicken Sternum Cartilage

| Tissue | Digestion time | 4-Hydroxyproline* | 5-Hydroxylysine* |
|---|---|---|---|
| Chicken Cartilage | 0 minutes | 0 | 0 |
|  | 45 minutes | 58 | 54 |
|  | 90 minutes | 73 | 65 |
|  | 180 minutes | 80 | 80 |
| Sturgeon Notochord | 0 minutes | 0 | 0 |
|  | 45 minutes | 84 | 82 |
|  | 90 minutes | 92 | 93 |
|  | 180 minutes | 102 | 100 |

*% of total HPro and HLys present in the undigested tissue.

Table 6 demonstrates that in simulated gastric fluid, notochord is solubilized at a rate that significantly exceeds the rate of chicken cartilage solubilization. Without being bound to a particular theory, it is believed that notochord is more readily solubilized by virtue of its less developed matrix of chondroitin sulphate chains, proteoglycans and polypeptides. Further, this data would suggest that notochord could potentially have an advantage over cartilage as an enterally administered toleragen since it is more readily solubilized by gastric juices. If notochord is more readily solubilized, it theoretically may reduce required dosages and/or expedite therapeutic impact.

The size exclusion chromatograph indicated for 0-time digests a peak at about 43 minutes for chicken cartilage which is essentially missing for notochord. At 45 minutes of digestion, the notochord and chicken cartilage digests begin to diverge substantially. For example, there are substantial peaks between about 30 minutes and 40 minutes for the notochord digest which are either missing or greatly reduced in the chicken cartilage digest. Most interesting is a peak at about 43 minutes wherein the notochord peak is about one fifth the size of the chicken cartilage peak. Similar differences also appear for the 90 and 180 minute digestion. This Experiment further demonstrates the substantial and significant differences between the sturgeon notochord and chicken cartilage.

Experiment 1.3: Trypsin Digestion

Pulverized preparations of chicken cartilage and notochord were suspended in 0.05 M TRIS buffer, pH 7.5, containing trypsin (Sigma Type XIII) at 1 mg/14 mg of dry tissue, and incubated at 37° C. for 4 hours. Each digest was filtered and the filtrates were "peptide mapped" by Reversed Phase HPLC using a Hewlett-Packard Model 1090M with Vydac C18 Protein and Peptide; 4.6×250 mm; 5 µm particle size column (The Separations Group; P/N 218TP54) and two mobile phases: Mobile Phase A was 0.08% trifluoroacetic acid in water and Mobile Phase B was 0.08% trifluoroacetic acid in acetonitrile. Injection volume of 25 µL flowed at 0.8 mL/minute at 40° C. for 90 minutes according to the following elution gradient. Detection was by U.V. absorbance at 214 nm and at 280 nm.

Gradient Elution Program

| Time in Minutes | % Mobile Phase B |
| --- | --- |
| 0 | 5 |
| 5 | 5 |
| 65 | 35 |
| 67 | 55 |
| 70 | 55 |
| 75 | 5 |
| 90 | stop |

A significant number of qualitative and quantitative differences were evidenced between the notochord and cartilage digests which indicates that the trypsin was cleaving the tissues at different locations. This fact indicates that the amino acid sequences are significantly different from each other in these tissues. More specifically, at 214 nm detection and at about 17 minutes, the chicken cartilage produced a peak that was more than twice the peak for sturgeon notochord at the same time. At 280 nm detection, the cartilage produced a peak at about 50 minutes that was at least an order of magnitude greater than the corresponding peak for notochord.

Experiment 1.4: Hexosamine Release

In this Experiment, trifluoroacetic acid (TFA) digests of chicken cartilage and sturgeon notochord were conducted to evaluate the galactosamine and glucosamine content of each tissue. Galactosamine and glucosamine are monomer components of GAG copolymer synthesis. Hexosamine contents may relate to an immunological or toleragen potential of a tissue.

Pulverized preparations of each tissue were hydrolyzed and the galactosamine and glucosamine released by each tissue was measured by HPLC as AQC (6-Aminoquinolyl-N-Hydroxysuccinimidyl Carbamate) derivatives. The hydrolysis was conducted for 14 hours at 120° C. in 1.35 M TFA. The galactosamine concentrations and their chondroitin sulfate-equivalents (chondroitin sulfate is a copolymer of N-acetyl-galactosamine sulfate and glucuronic acid), as well as the glucosamine concentrations and their hyaluronic acid equivalents (hyaluronic acid is a copolymer of N-acetyl-glycosamine and glucuronic acid) are presented in Table 7. The hexosamines released by TFA hydrolysis were separated and detected by HPLC using a Hewlett-Packard Model 1090M and a Brownlee Spher-5 RP-8; 4.6×250 nm; 5 µm particle size column (Alltech P/N 141033) and two mobile phases: Mobile Phase A was 0.15 M sodium acetate, 0.019 M triethylamine, 10 mg/L disodium EDTA; pH 5.0; and Mobile Phase B was 70 volumes A+30 volumes acetonitrile. Injection volume of 20 µL flowed at 0.6 mL/minute at 40° C. for 50 minutes according to the following elution gradient. Detection was by U.V. absorbance at 248 nm.

Gradient Elution Program:

| Time in Minutes | % Mobile Phase B |
| --- | --- |
| 0 | 0 |
| 5 | 23 |
| 25 | 23 |
| 27 | 100 |
| 32 | 100 |
| 35 | 0 |
| 50 | stop |

This experiment is one means of comparing the proteoglycan content of each tissue which is an approximate measure of its character as an immunogen/toleragen. The data presented in Table 7 clearly illustrate the difference in the two tissues.

TABLE 7

Hexosamine Release Comparison
Sturgeon Notochord vs. Chicken Sternum Cartilage
Hexosamine Released per gram of Dry Tissue*

| Saccharide | Chicken Cartilage (mg) | Sturgeon Notochord (mg) |
| --- | --- | --- |
| Galactosamine | 55 | 114 |
| Glucosamine | 105 | 19 |
| Chondroitin SO$_4$ equivalents | 147 | 303 |
| Hyaluronic Acid equivalents | 234 | 42 |

*- Hydrolysis - 14 hours at 120° C. in 1.35M TFA

In conclusion, the data presented in Experiments 1.1 to 1.4 evidences a number of significant differences between chicken cartilage and sturgeon notochord: (1) amino acid composition; (2) peptides from hydrolysis based on simulated gastric fluid digestion; (3) amino acid sequence based on trypsin digestion; and (4) proteoglycan content. In addition, collagen purified from sturgeon notochord was significantly different from bovine CII.

In spite of the above demonstration that sturgeon notochord and its collagen is qualitatively and quantitatively different from chicken cartilage and CII found within, the present inventors believed that investigating notochord efficacy was warranted as sturgeon notochord is highly digestible, low in cost, and is available from a highly controlled environment. The following Examples compare the activity of sturgeon notochord and collagen derived therefrom against various collagen-containing tissues, including chicken cartilage. All following examples were conducted in accordance with the current guidelines for animal welfare.

Example II: Protective Effect

2.1 Protective Effect of Sturgeon Notochord

These Examples were conducted to investigate the effectiveness of sturgeon notochord in protecting mice from collagen-induced arthritis (CIA). Female DBA/1 Lac J strain mice, approximately 6–8 weeks of age, were obtained from Jackson Laboratories of Bar Harbor, Me. Three groups of 20 mice per group were acclimated to their surroundings for 7 days. A standard mouse chow (Purina Certified Mouse Chow #5015; 11% by wt. fat; collagen-free) and water were provided for ad libitum consumption to all animals.

On Days −10, −7, −5 and −2 prior to immunization, mice were sensitized by one of three test compositions; bovine serum albumin (BSA, a tolerogenically inert protein in CIA), cod skin gelatin, or sturgeon notochord. Bovine serum albumin (a protein derived from non-connective tissue) and cod skin gelatin (a protein derived from another connective tissue containing Type I collagen of a fish) served as negative controls. Sturgeon notochord was obtained from farm raised sturgeon and pulverized in liquid nitrogen. The level of each test composition was equilibrated to a 300 µg protein dose based on protein (including collagen) content. Test articles were dissolved/suspended in 0.01 M acetic acid and 0.3 ml was administered per dose to each mouse with a ball tipped feeding needle.

| Group | Treatment | (mg/dose) |
|---|---|---|
| 1 | BSA (91.7% protein, 0% collagen) | 0.33 |
| 2 | Cod skin gelatin (93.6% protein, 93.6% Type I collagen) | 0.32 |
| 3 | Sturgeon notochord (10% protein, 8.5% collagen) | 3.53 |

On Day 0, the mice were immunized at the base of the tail with 100 µg of bovine CII which was emulsified in Complete Freund's Adjuvant (CFA). On Day 7, a second booster dose of 100 µg bovine CII in CFA was administered by the same route. On Day 14, the mice were injected subcutaneously with 100 µg of lipopolysaccharide (LPS). This protocol represents a mild induction of CIA.

Mice were inspected daily for the onset of CIA, characterized by erythema and edema. Limbs were clinically evaluated and graded on a scale of 0 to 3 (0, absence of arthritis; 1, mild swelling and erythema; 2, swelling and erythema of both tarsus and ankle; 3, ankylosis and bone deformity). Mice that did not develop arthritis were marked negative for arthritis. All mice were euthanized by $CO_2$ on Day 50.

On Days 20, 28, 40 and 50, the group fed with sturgeon notochord consistently had fewer animals with CIA than those fed BSA or cod skin gelatin (Table 8). The % onset calculated based on the Day 50 data showed that 78% and 79% of mice fed BSA and cod skin gelatin, respectively, had CIA whereas only 58% of mice fed sturgeon notochord evidenced CIA. Furthermore, the median day of CIA onset for the group fed sturgeon notochord was delayed by 13 days compared to the negative control groups. The mean severity score was highest for the group fed cod skin gelatin followed by the BSA-fed group, and the sturgeon notochord-fed group had the lowest severity score. The data herein suggest that sturgeon notochord is effective in delaying and attenuating CIA compared to BSA or cod skin gelatin.

TABLE 8

| | # of animals | | # animals with arthritis | | | | % | median day of | mean severity |
|---|---|---|---|---|---|---|---|---|---|
| Treatment | dead | alive | Day 20 | Day 28 | Day 40 | Day 50 | onset* | onset | score** |
| BSA | 2 | 18 | 12 | 12 | 12 | 14 | 78 | 17 | 2.05 |
| Cod skin gelatin | 1 | 19 | 14 | 14 | 14 | 15 | 79 | 17 | 2.40 |
| Sturgeon notochord | 1 | 19 | 9 | 10 | 1 | 11 | 58 | 30 | 1.99 |

*Calculated based on the Day 50 data
**Based on Day 20, 29, 34, 43 and 50 data which allowed the most data points for all groups.

2.2 Protective Effect of Sturgeon Notochord-Stronger Induction of CIA

To evaluate the effectiveness of sturgeon notochord in protecting mice from CIA, this experiment was conducted in a manner similar to Example 2.1 except that the immunization protocol was slightly modified. The experimental protocol employed in this experiment represents a stronger induction of CIA compared to that of Example 2.1.

The mice were DBA/1 Lac J strain supplied by Jackson Laboratories of Bar Harbor, Me. All mice were female and about 6–8 weeks of age. Three groups of 15–18 mice per group were acclimated to their surroundings for 7 days. A standard mouse chow and water were provided for ad libitum consumption.

On Days −10, −7, −5 and −2 prior to immunization, mice were sensitized by one of three test samples: 1) vehicle; 2) cod skin gelatin; and 3) sturgeon notochord. Cod skin gelatin (Type I collagen) was used as a negative control. Sturgeon notochord was obtained from farm-raised sturgeon and pulverized in liquid nitrogen as previously described. The level of each test composition was equilibrated to a 300 µg collagen per dose. Test compositions were dissolved/suspended in 0.01 M acetic acid and 0.3 ml was administered to each mouse with a ball tipped feeding needle.

| Group | Treatment | (mg/dose) |
|---|---|---|
| 1 | Vehicle (0.01M acetic acid) | 0 |
| 2 | Cod skin gelatin (93.6% protein, 93.6% Type I collagen) | 0.32 |
| 3 | Sturgeon notochord (10% protein, 9.5% collagen) | 3.16 |

On Day 0, the mice were immunized at the base of the tail with 100 µg of bovine CII which was emulsified in CFA. On Day 14, five animals from each group were bled retroorbitally and anti-type II collagen antibody titer in the serum was analyzed by an ELISA method to confirm that the animals were primed. On Day 21, the mice were injected subcutaneously with 50 µg of LPS.

TABLE 9

Day 14 Type II Collagen Antibody Titer - 1:1000 Dilution

| Treatment | n | Mean Antibody Titer* | % Change from Control |
|---|---|---|---|
| Vehicle | 5 | 0.89 ± 0.27 | — |
| Cod skin gelatin | 4 | 0.57 ± 0.23 | −37 |
| Sturgeon notochord | 5 | 0.22 ± 0.05 | −76 |

*- The average value for non-immunized animals was 0.03.

The CII antibody titer for the vehicle-fed immunized mice increased to 0.89±0.27 compared to the average CII antibody titer for non-immunized mice of 0.03. This indicates that animals were primed by CII immunization. On the other hand, those mice tolerized with sturgeon notochord showed significant reduction (−76%) in the CII antibody titer, which suggests that their immune system was de-sensitized compared to the vehicle-fed group. These findings are in agreement with the antibody data of Nagler-Anderson, et al., "Suppression of Type II Collagen-Induced Arthritis by Intragastric Administration of Soluble Type II Collagen", *Proc. Natl Acad, Sci,* U.S.A., 1986:83;7443–7446 and the clinical findings set forth in Table 10. Although there was some reduction over the vehicle control, the reduction seen in the cod skin gelatin fed group was not significant.

Mice were inspected daily for the onset of CIA, characterized by erythema and edema. Limbs were clinically evaluated and graded on a scale of 0 to 6 (0, absence of arthritis; 0.5, one or more digits swollen or only the paw swollen; 1, entire paw swollen; 2, entire paw severely swollen; 3, mild deformity after inflammation subsides; 4, severe deformity; 5, mild ankylosis with partial loss of joint function in the paw; 6, severe ankylosis with total loss of joint function in the paw). All mice were euthanized by $CO_2$ on Day 35.

TABLE 10

| Treatment | n | % of incidence | | | severity score* | | |
|---|---|---|---|---|---|---|---|
| | | D25 | D28 | D35 | D25 | D28 | D35 |
| Vehicle | 18 | 94 | 89 | 83 | 4.67 ± 0.64[ab] | 7.14 ± 1.09 | 10.00 ± 1.66[a] |
| Cod Skin Gelatin | 18 | 89 | 89 | 94 | 5.53 ± 0.57[a] | 8.61 ± 0.85 | 10.67 ± 1.18[a] |
| Sturgeon notochord | 15 | 87 | 87 | 93 | 3.73 ± 0.68[b] | 6.40 ± 1.14 | 5.83 ± 1.30[b] |

*Values in columns with different superscript letters represent significant differences with P < 0.05.

The % incidence of CIA was higher across all treatments compared with Example 2.1, confirming the harsh nature of the CIA induction protocol employed in this Example. Nevertheless, the group fed sturgeon notochord had significantly lower (P<0.05) severity scores than those fed vehicle or cod skin gelatin. These findings are consistent with the results of Example 2.1 which indicate that sturgeon notochord is effective in attenuating CIA.

Example III

Sturgeon Notochord vs. Chicken Cartilage

This experiment was conducted to compare the effectiveness of chicken cartilage and sturgeon notochord in protecting mice from CIA. This Experiment was conducted in a manner similar to Example II.

The treatment groups were as follows:

| Group | Treatment | (mg/dose) |
|---|---|---|
| 1 | vehicle (0.01M acetic acid) | 0 |
| 2 | vehicle + chicken cartilage (17% protein, 13.6% CII) | 2.21 |
| 3 | vehicle + sturgeon notochord (10% protein, 9.5% collagen) | 3.16 |

Group 1 served as the control. Chicken cartilage (xiphoid cartilage on the sternum) was obtained from a commercial source and was pulverized in liquid nitrogen and used for Group 2. Sturgeon notochord as described previously was used for Group 3. The dose level (300 µg/dose) was selected based on previous data.

The sensitization procedure consisted of dissolving/suspending each sample in 0.01 M acetic acid and 0.3 ml was administered to each mouse with a ball tipped feeding needle on Days −10, −7, −5 and −2 prior to immunization. On Day 0, the mice were immunized at the base of the tail with 100 µg of bovine CII which was emulsified in CFA. On Day 21, the mice were injected, subcutaneously, with 50 µg of LPS.

Body weights for each mouse were recorded on Day 0, 21, 28 and 35. Mice were inspected daily for the onset of CIA, which was characterized by erythema and edema. Limbs were clinically evaluated and graded on a scale of 0 to 6, as previously described.

The data presented in Table 11 demonstrates that sturgeon notochord is efficacious in attenuating CIA. In fact, the sturgeon notochord fed group was the only group that was significantly (p<0.05) different from the control group in the severity score. There was a numerical improvement in the severity score by chicken cartilage, but it was not significantly different from the control group.

TABLE 11

Tolerizing Effect of Chicken Cartilage and Sturgeon Notochord on Mouse Developing CIA - Day 35

| Treated Groups | n | % incidence | Severity Score Mean ± SE | % Change From Control | % Wt. Change From Day 21 |
|---|---|---|---|---|---|
| 1: 0.01M acetic acid | 18 | 83 | 10.0 ± 1.7[a] | — | −3 |
| 2: Chicken Cartilage | 14 | 86 | 6.6 ± 1.6[a,b] | −34 | −10 |
| 3: Sturgeon Notochord | 15 | 93 | 5.8 ± 1.3[b] | −42 | +3 |

[a,b]Numbers with different alphabetical superscripts are significantly different from each other at a value of P < 0.05.

Furthermore and most importantly, Table 11 surprisingly evidences that the only group to gain weight was the sturgeon notochord group. The chicken cartilage actually evidenced a weight loss of 10%. When animals are subjected to trauma or sick from diseases, they typically reduce their feed intake which results in weight loss as seen herein in the chicken cartilage group. Thus, this data further supports the inventors' belief that sturgeon notochord is not at all similar to chicken cartilage and in fact may be better.

Example IV

Dose Response

To evaluate the dose response of sturgeon notochord in protecting mice from CIA, this experiment was conducted in a manner similar to Examples II and III. The mice were DBA/1 Lac J strain supplied by Jackson Laboratories of Bar Harbor, Me. All mice were female and about 6–8 weeks of age. Eight groups of 10–15 mice per group were acclimated to their surroundings for 7 days. A standard mouse chow and water were provided for ad libitum consumption to all animals.

On Days −10, −7, −5 and −2 prior to immunization, mice were sensitized by sturgeon notochord. A group fed only vehicle was used as the negative control and a group fed with an effective dose of dexamethasone (0.1 mg/kg per os) was used as the positive control. Sturgeon notochord was obtained from farm raised sturgeon and pulverized in liquid nitrogen. The dose level of sturgeon notochord was equilibrated to 1, 3, 10, 30, 100 or 300 µg of collagen per dose based on the protein and collagen content. Sturgeon notochord was dissolved/suspended in 0.01 M acetic acid and 0.3 ml was administered to each mouse with a ball tipped feeding needle.

| Group | Treatment | Dose |
|---|---|---|
| 1 | Vehicle (0.01M acetic acid) | |
| 2 | Dexamethasone | 0.1 mg/kg p.o. |
| 3 | Sturgeon notochord (10% protein, 9.5% collagen) | 0.0105 mg |
| 4 | Sturgeon notochord | 0.032 mg |
| 5 | Sturgeon notochord | 0.105 mg |
| 6 | Sturgeon notochord | 0.316 mg |
| 7 | Sturgeon notochord | 1.053 mg |
| 8 | Sturgeon notochord | 3.160 mg |

On Day 0, the mice were immunized at the base of the tail with 100 µg of bovine CII which was emulsified in CFA. On Day 21, the mice were injected subcutaneously with 50 µg of LPS.

Mice were inspected daily for the onset of CIA, characterized by erythema and edema. Limbs were clinically evaluated and graded on a scale of 0 to 6 as described in Example III.

Dexamethasone (an agent known to reduce CIA) significantly reduced both % of incidence and severity score (Table 12). The % incidence of CIA was also reduced in all groups fed sturgeon notochord, regardless of the dose level (except Day 35 at 3.160 mg/dose group). Severity score was also reduced in all sturgeon notochord fed groups in a dose-dependent manner on Day 26. Moreover, the group fed 1.053 mg sturgeon notochord per dose significantly ($P<0.05$) reduced the severity score on Day 35 (a 50% reduction) and a 20% reduction in % incidence. These findings are consistent with the results of previous Examples that sturgeon notochord is effective in attenuating CIA.

TABLE 12

| | | Dose Study | | | | | |
|---|---|---|---|---|---|---|---|
| | | % of incidence | | | severity score | | |
| Treatment | n | D26 | D28 | D35 | D26 | D28 | D35 |
| Vehicle | 15 | 100 | 100 | 100 | 4.3 ± 0.5 | 6.2 ± 0.8 | 8.8 ± 0.9 |
| Dexamethasone | 10 | 40 | 50 | 50 | 1.0 ± 0.4* | 1.1 ± 0.4* | 1.1 ± 0.4* |
| Sturgeon notochord (0.0105 mg) | 10 | 80 | 80 | 80 | 3.5 ± 0.8 | 5.2 ± 1.3 | 6.8 ± 1.7 |

TABLE 12-continued

| | | Dose Study | | | | | |
|---|---|---|---|---|---|---|---|
| | | % of incidence | | | severity score | | |
| Treatment | n | D26 | D28 | D35 | D26 | D28 | D35 |
| Sturgeon notochord (0.032 mg) | 10 | 70 | 70 | 70 | 3.2 ± 1.0 | 4.7 ± 1.5 | 6.7 ± 2.1 |
| Sturgeon notochord (0.105 mg) | 9 | 89 | 89 | 89 | 2.7 ± 0.8 | 3.4 ± 1.2 | 5.2 ± 1.4 |
| Sturgeon notochord (0.316 mg) | 9 | 67 | 78 | 78 | 2.8 ± 1.1 | 4.3 ± 1.1 | 5.9 ± 2.1 |
| Sturgeon notochord (1.053 mg) | 10 | 80 | 80 | 80 | 2.5 ± 0.9 | 3.6 ± 1.4 | 4.4 ± 1.8* |
| Sturgeon notochord (3.160 mg) | 10 | 90 | 89 | 100 | 2.3 ± 0.4 | 4.4 ± 1.0 | 6.6 ± 1.7 |

*($P < 0.05$) from the vehicle fed control.

The inventors continued to observe four selected groups (vehicle control group, sturgeon notochord 0.105 mg/dose group, sturgeon notochord 1.053 mg/dose group, and dexamethasone group) until Day 79. Severity scores plotted against days post-sensitization are found in FIG. 1.

From the data generated, it is evident that the vehicle-fed control group showed a normal disease progression while dexamethasone was able to significantly suppress the severity score. The suppressive effect of sturgeon notochord lasted to Day 79 in the group fed 1.053 mg/dose. The group fed with 0.105 mg/dose also showed similar effect up to Day 70.

Example V

Sturgeon Collagen

This experiment was conducted to show the effect of collagen isolated from sturgeon notochord in protecting mice from CIA. This Experiment was conducted in a manner similar to Examples II, III, and IV.

The mice were DBA/1 Lac J strain supplied by Jackson Laboratories of Bar Harbor, Me. All mice were female and about 6–8 weeks of age. Three groups of 10–15 mice per group were acclimated to their surroundings for 7 days. Standard mouse chow and water were provided for ad libitum consumption to all animals.

On Days −10, −7, −5 and −2 prior to immunization, mice were sensitized by notochord collagen. Sturgeon notochord was obtained from farm raised sturgeon and collagen was extracted and purified by the method described in Eyre and Muir, "The Distribution of Different Molecular Species of Collagen in Fibrous, Elastic and Hyaline Cartilages of the Pig" *Biochem J* (1975) 151;595–602. Notochord collagen was dissolved/suspended in 0.01 M acetic acid and 0.3 ml was administered to each mouse with a ball tipped feeding needle. The dose levels tested were 30 or 100 µg per dose per animal.

| Group | Treatment | Collagen Dose |
|---|---|---|
| 1 | Vehicle (0.01M acetic acid) | |
| 2 | Sturgeon notochord collagen (60% collagen) | 30 µg |
| 3 | Sturgeon notochord collagen (60% collagen) | 100 µg |

On Day 0, the mice were immunized at the base of the tail with 100 µg of bovine CII which was emulsified in CFA. On Day 21, the mice were injected subcutaneously with 50 µg of LPS.

Mice were inspected daily for the onset of CIA, characterized by erythema and edema. Limbs were clinically evaluated and graded on a scale of 0 to 6 as previously described. Table 13 sets forth the results from this experiment.

TABLE 13

| Treatment | n | % incidence D25 | % incidence D35 | severity score D25 | severity score D35 | % weight change (D35 vs. D21) |
|---|---|---|---|---|---|---|
| Vehicle | 10 | 100 | 100 | 3.2 ± 0.4 | 6.4 ± 1.2 | 0 |
| Sturgeon notochord collagen (30 µg) | 10 | 100 | 100 | 2.3 ± 0.7 | 3.7 ± 1.2 | +4 |
| Sturgeon notochord collagen (100 µg) | 9 | 89 | 89 | 3.1 ± 0.6 | 5.0 ± 1.4 | +4 |

Severity scores were reduced in both groups fed sturgeon notochord collagen. The group fed 30 µg showed a 42% reduction in the severity score on Day 35 compared to the vehicle-fed control group. The group fed 100 µg showed a decrease in the percentage of incidence. This is consistent with previously published data by Zhang Z J, C S Y Lee, O Lider, H L Weiner. "Suppression of Adjuvant Arthritis in Lewis Rats by Oral Administration of Type II Collagen", *J. Immuno* (1990), 145; 2489–2493. It was also observed that both groups fed with sturgeon notochord collagen evidenced an increase in body weight.

Example VI: Protective Effect in Chronic Arthritis

Effect of Sturgeon Notochord in a Chronic Arthritis Induced by Human Type II Collagen This experiment was conducted to investigate the effectiveness of sturgeon notochord in protecting mice from chronic CIA induced by using human CII (unlike other examples in this application which used bovine CII). Female DBA/1 Lac J strain mice, approximately 6–8 weeks of age, were obtained from Jackson Laboratories of Bar Harbor, Me. Animals were acclimated to their surroundings for 7 days. A standard mouse chow (Teklad diet) and water were provided for ad libitum consumption.

The chronic CIA induction was achieved by immunizing each mice on Day 0 and Day 21 at the base of the tail with 50 mg of human CII which was emulsified in CFA. Animals in the vehicle control group and Dexamethasone control group received 0.01 M acetic acid on Days –10, –7, –5, and –2 and 0.1 mg dexamethasone/kg BW on Days 21 and 35, respectively. The mice receiving sturgeon notochord were divided into three groups and they were dosed with 100 mg collagen per dose dissolved/suspended in 0.01 M acetic acid and 0.3 ml was administered. Group 1 received sturgeon notochord on Days –10, –7, –5, and –2; Group 2, on Days 7, 10, 12, and 14; Group 3, Days 28, 31, 33, and 35.

Mice were inspected daily for the onset of CIA, characterized by erythema and edema. Limbs were clinically evaluated and graded on a scale of 0 to 6 (0, absence of arthritis; 0.5, one or more digits swollen or only the paw swollen; 1, entire paw swollen; 2, entire paw severely swollen; 3, mild deformity after inflammation subsides; 4, severe deformity; 5, mild ankylosis with partial loss of joint function in the paw; 6, severe ankylosis with total loss of joint function in the paw). All mice were euthanized by $CO_2$ on Day 35.

| Treatment | n | % incidence D28 | % incidence D35 | % incidence D42 | % incidence D49 | severity score D28 | severity score D35 | severity score D42 | severity score D49 |
|---|---|---|---|---|---|---|---|---|---|
| Vehicle | 11 | 36 | 73 | 82 | 82 | 1.14 | 1.95 | 3.18 | 5.41 |
| Group 1 | 12 | 58 | 75 | 75 | 75 | 0.63 | 2.21 | 3.42 | 4.50 |
| Group 2 | 12 | 50 | 58 | 67 | 75 | 0.83 | 1.13 | 1.58 | 2.58 |
| Group 3 | 11 | 45 | 73 | 91 | 90 | 1.05 | 2.23 | 2.09 | 4.05 |
| Dex | 6 | 33 | 67 | 100 | 100 | 0.25 | 0.42 | 1.75 | 3.58 |

All groups dosed with sturgeon notochord had lower severity score than the vehicle control group. Particularly Group 2 was very effective in suppressing both % incidence and the severity score (a 52% reduction on Day 49) compared to the vehicle control group. These findings are consistent with the results of LPS-potenciated CIA, but moreover, they illustrated that sturgeon notochord is effective in a chronic CIA model and in a non-antigen independent manner. The model used and the results herein may implicate that sturgeon notochord may be effective in the chronic human rheumatoid arthritis. Industrial Applicability The medical community is constantly searching for improved treatments for arthritis. This invention provides for the use of notochord and its extracts (i.e., notochord collagen) for oral administration to lessen the onset of arthritis and to reduce the intensity of the disease. Sturgeon notochord, is particularly suited for inclusion into nutritional formulas and supplements. Further, sturgeon notochord is inexpensive and of abundant and reliable supply. Various modifications may be made in the present invention without departing from the spirit or scope thereof, as will be readily apparent to those skilled in the art.

We claim:

1. A composition useful for oral consumption by mammals comprising at least one component which includes extracts of chordate notochord, wherein said extract is notochord glucosamine.

2. The composition of claim 1 wherein said composition is in a solid dosage form containing from 1.0 µg to 2.0 gms of said component.

3. The composition of claim 2 wherein said solid dosage form is in the form of a tablet, capsule, pill or powder.

4. The composition of claim 3 wherein said tablet, capsule or pill contains from 50 µg to 500 mg of said component.

5. The composition of claim 1 wherein said composition is in liquid form containing said component at a concentration of from 10 µg to 700 gms per liter.

6. A solid dosage form useful for oral consumption by a mammal comprising a component selected from the group consisting of sturgeon notochord, extracts of sturgeon notochord, and mixtures thereof, wherein said solid dosage form is a tablet, pill, or capsule.

7. The solid dosage form of claim 6, wherein said solid dosage form contains from 1.0 µg to 2.0 gms of said component.

8. The solid dosage form of claim 6 wherein said dosage form contains from 50 µg to 500 mg of said component.

* * * * *